(12) United States Patent
Pinhasi et al.

(10) Patent No.: US 6,703,044 B1
(45) Date of Patent: Mar. 9, 2004

(54) VENLAFAXINE FORMULATIONS

(75) Inventors: Adel Pinhasi, Holon (IL); Mila Gomberg, Jerusalem (IL); Avi Avramoff, Haifa (IL)

(73) Assignee: Dexcel Pharma Tech, Ltd, Jerusalem (IL)

( * ) Notice: Subject to any disclaimer, the term of this patent is extended or adjusted under 35 U.S.C. 154(b) by 0 days.

(21) Appl. No.: 10/280,084

(22) Filed: Oct. 25, 2002

(51) Int. Cl.[7] .................. A61K 9/48; A61K 31/135; A01N 33/04; C07C 215/42
(52) U.S. Cl. .................. 424/452; 424/463; 514/653; 564/360
(58) Field of Search .................. 514/653; 564/360; 424/452, 463

(56) References Cited

U.S. PATENT DOCUMENTS

| | | |
|---|---|---|
| 4,138,475 A | 2/1979 | McAinsh et al. |
| 4,389,393 A | 6/1983 | Schor et al. |
| 4,535,186 A | 8/1985 | Husbands et al. |
| 4,966,768 A | 10/1990 | Michelucci et al. |
| 5,840,332 A | 11/1998 | Lerner et al. |
| 6,274,171 B1 | 8/2001 | Sherman et al. |
| 6,403,120 B1 | 6/2002 | Sherman et al. |
| 6,419,958 B2 | 7/2002 | Sherman et al. |
| 2001/0055612 A1 | 12/2001 | Sherman et al. |
| 2002/0025339 A1 | 2/2002 | Sherman et al. |

*Primary Examiner*—Brian Davis
(74) *Attorney, Agent, or Firm*—Foley & Lardner

(57) ABSTRACT

The invention provides a method for treating a subject with venlafaxine, comprising administering to the subject a formulation having a therapeutically effective amount of venlafaxine or a pharmaceutically acceptable salt thereof, wherein the formulation provides a delayed burst release after at least three hours resulting in dispersion mainly through the colon of the active ingredient into the blood stream as a result of colon absorption over a period of at least 24 hours.

63 Claims, 11 Drawing Sheets

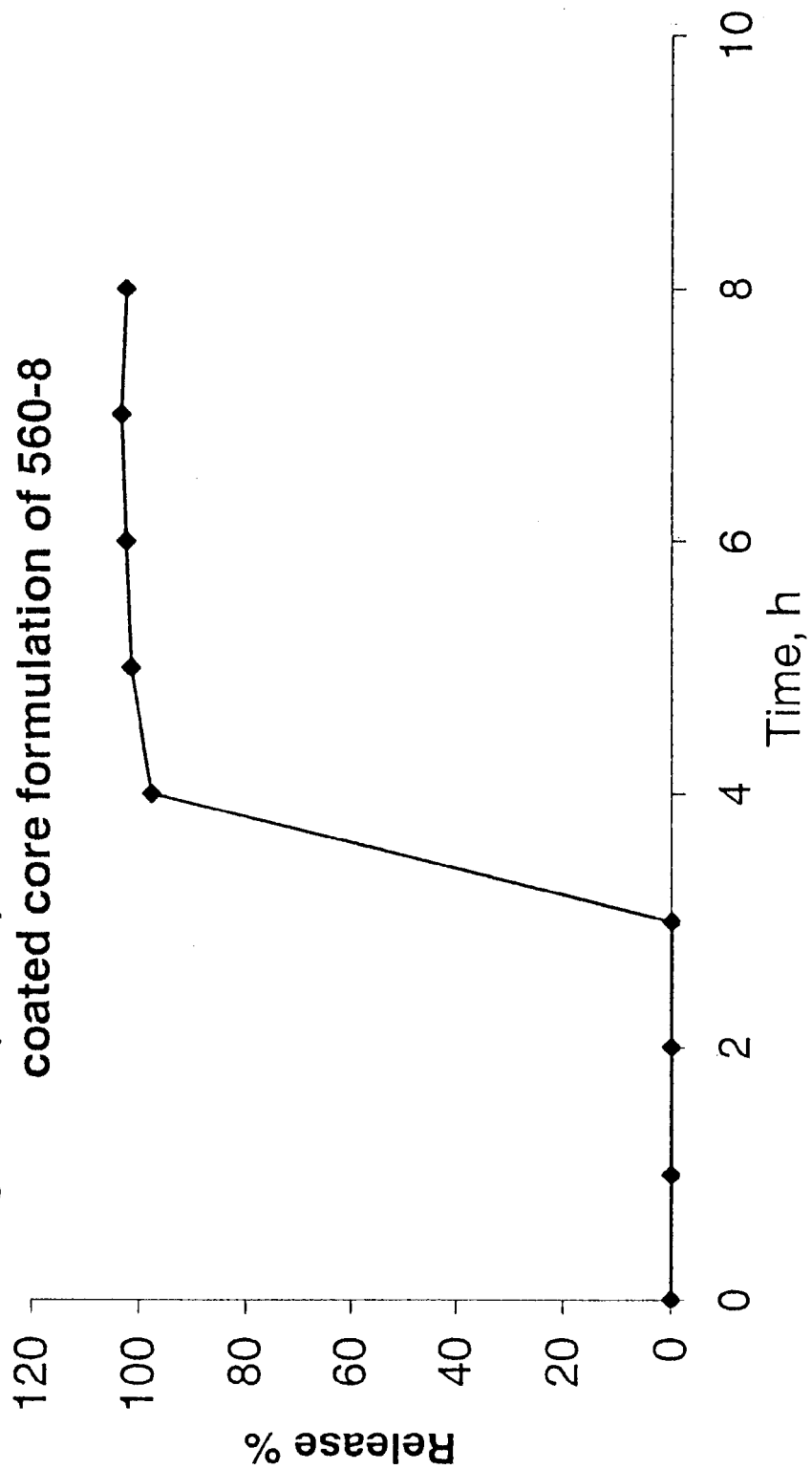

Figure 2 (560-12): The release of VLF from TCDS-coated core formulation of 560-11

Figure 3 (560-16): The release of VLF from TCDS-coated core formulation of 560-15

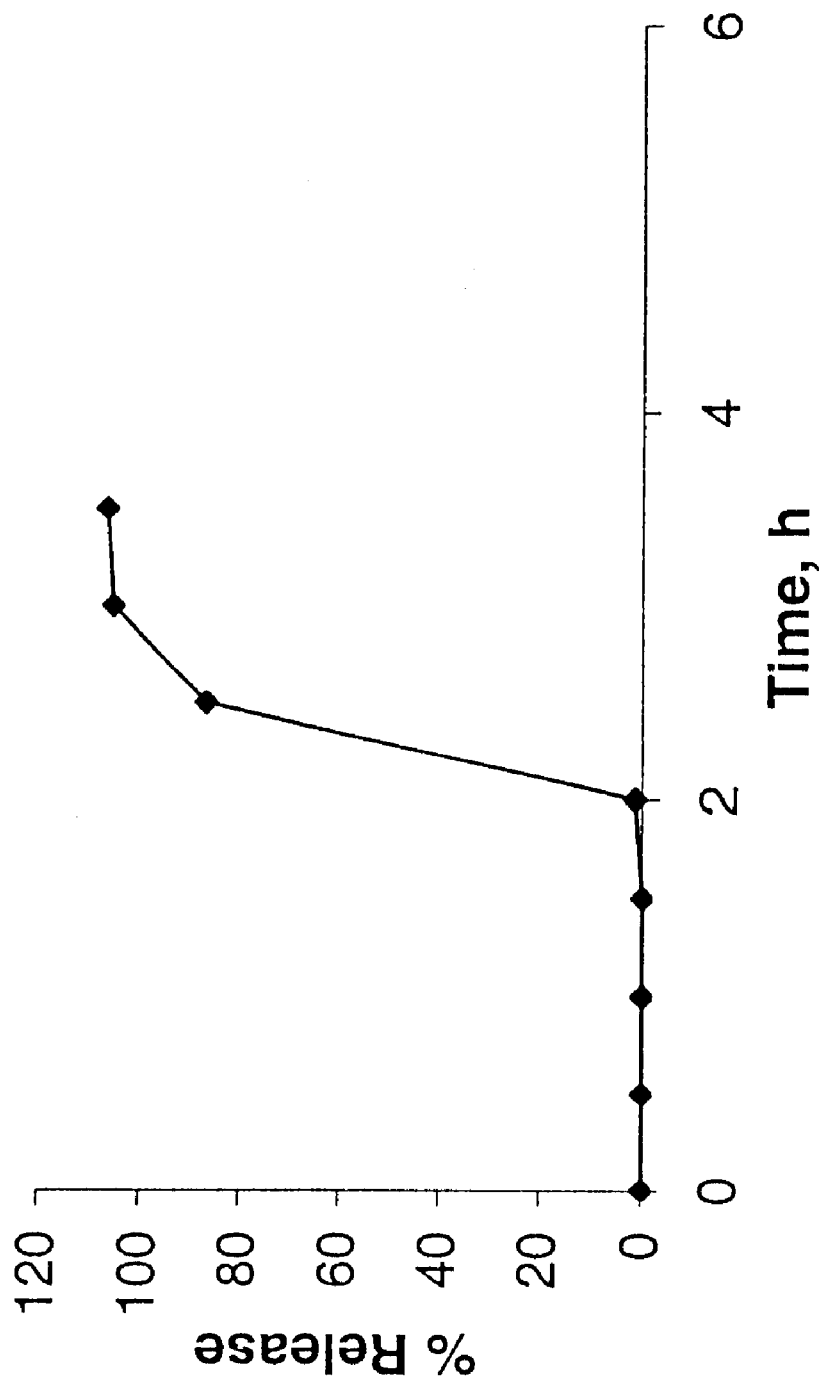
Figure 4 (560-24A): The release of VLF from TCDS-coated core formulation of 560

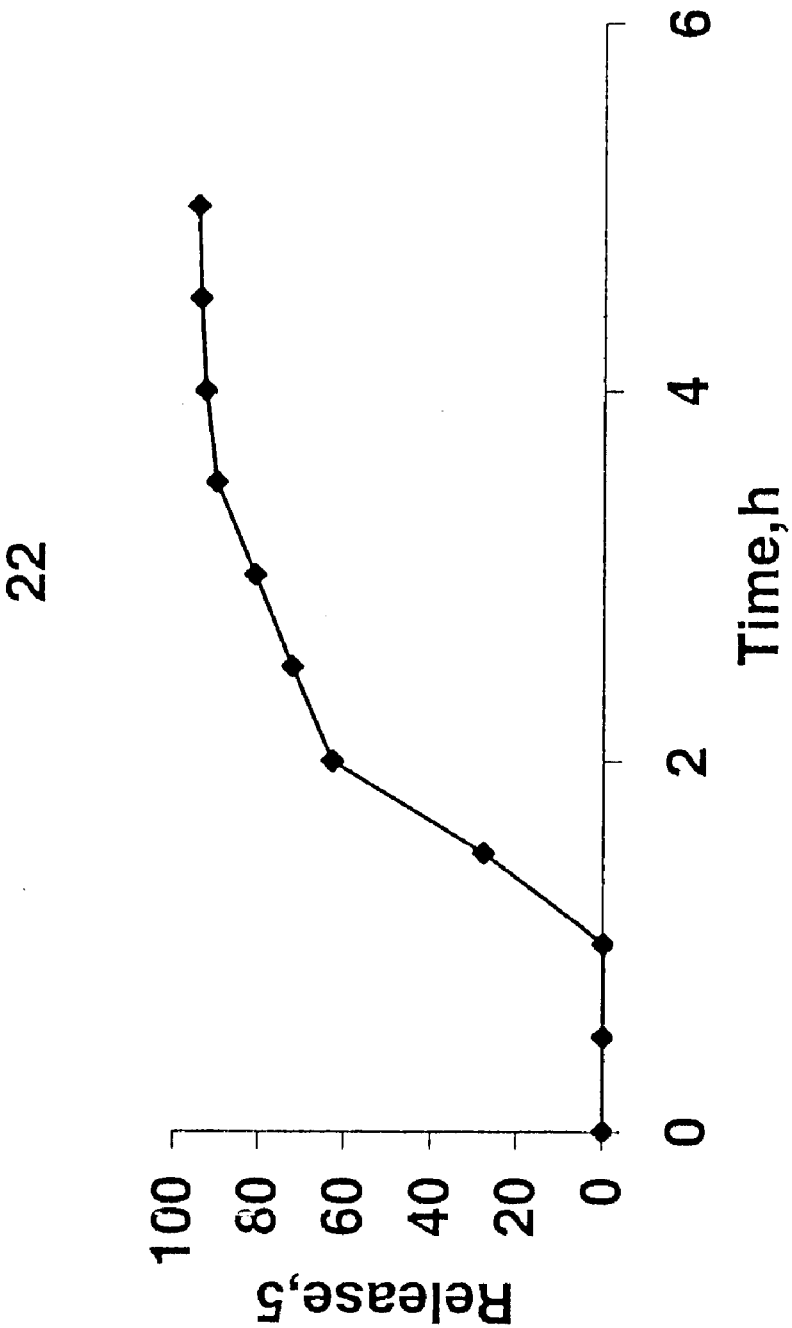
Figure 5 (560-24B): The release of VLF from TCDS-coated of the core formulation of 560-22

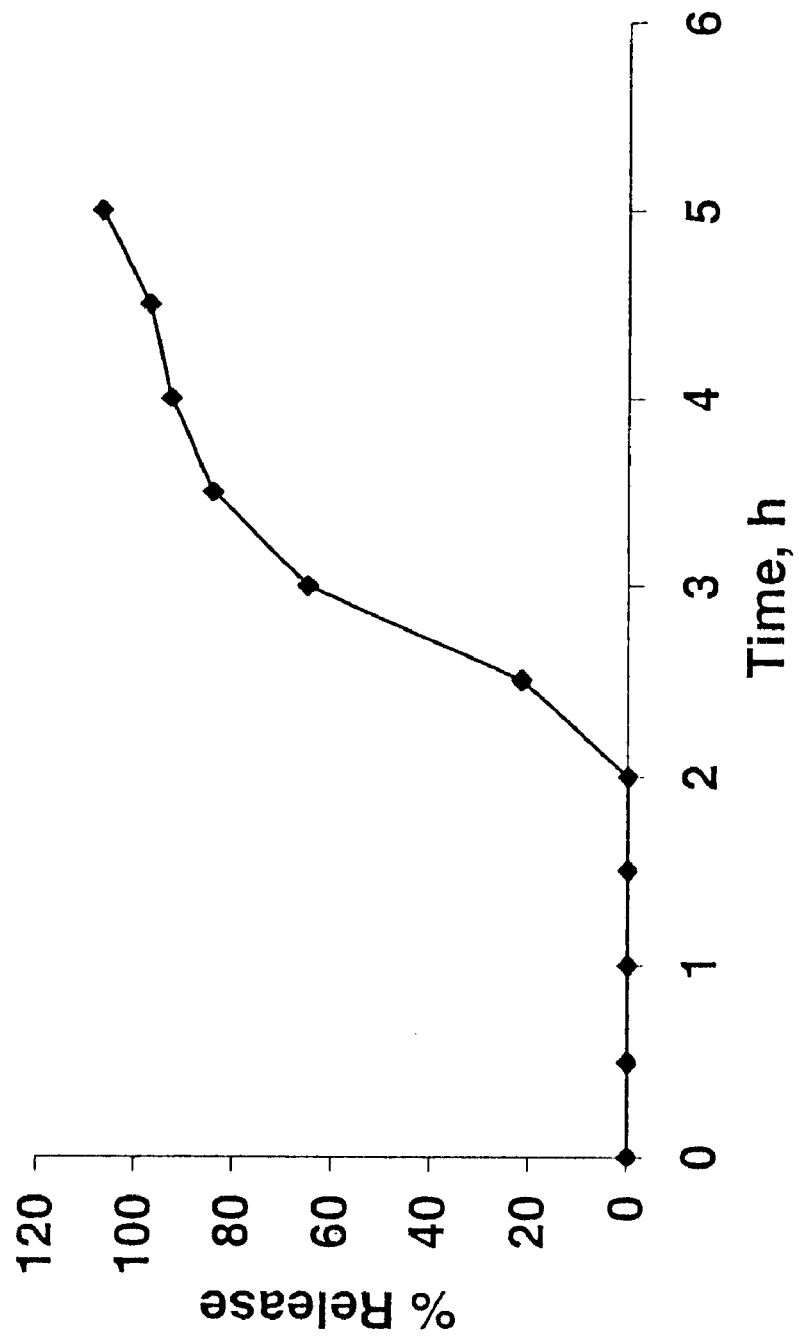

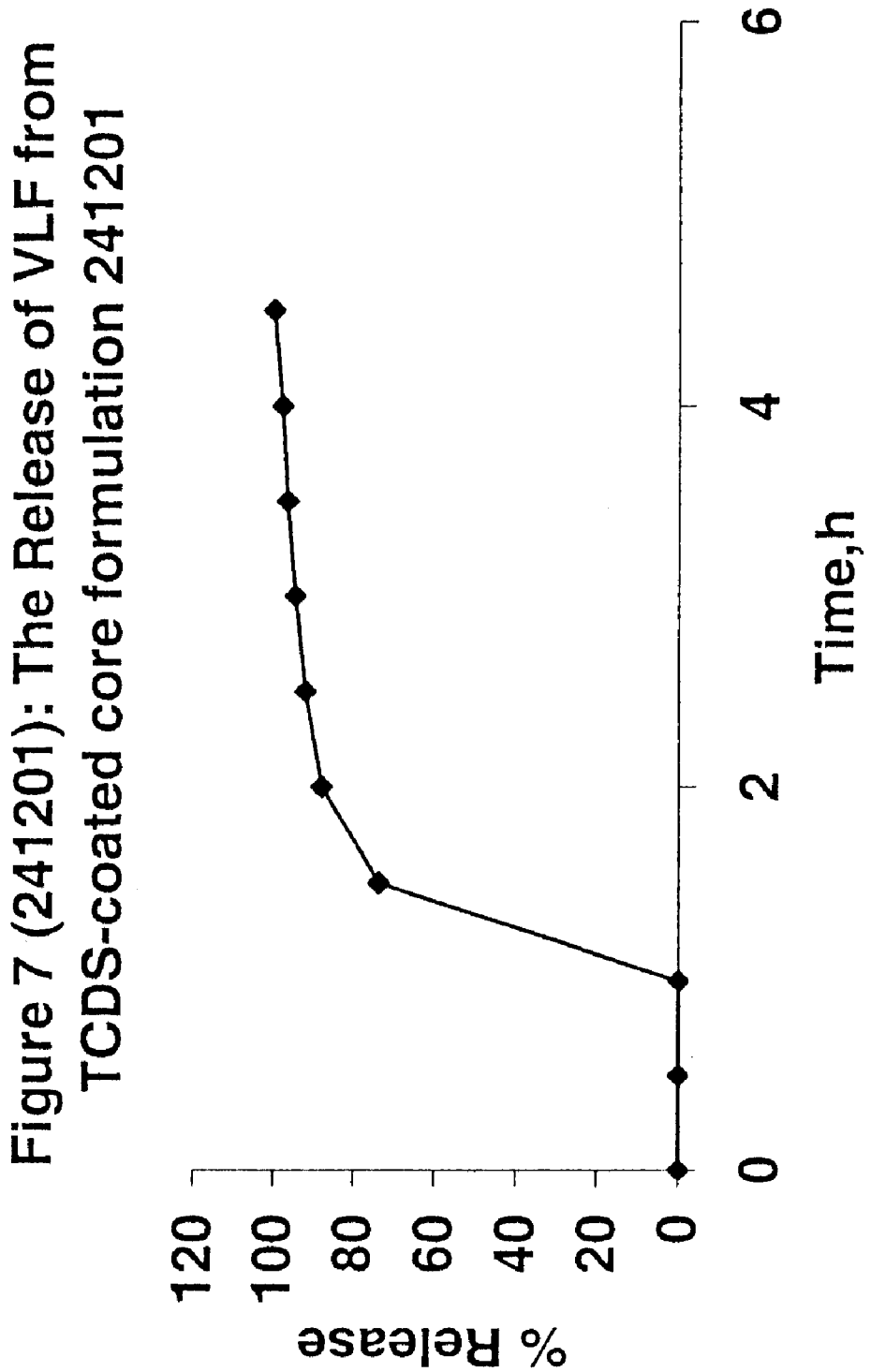
Figure 7 (241201): The Release of VLF from TCDS-coated core formulation 241201

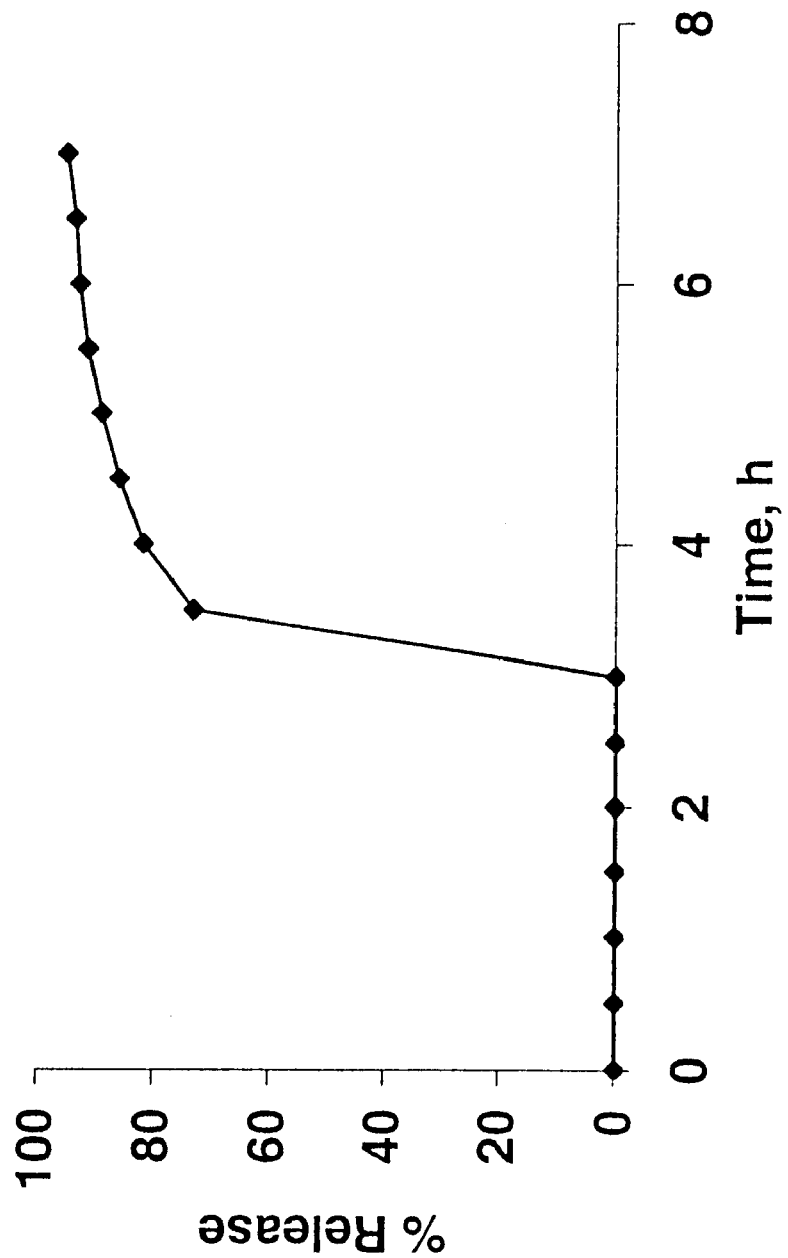

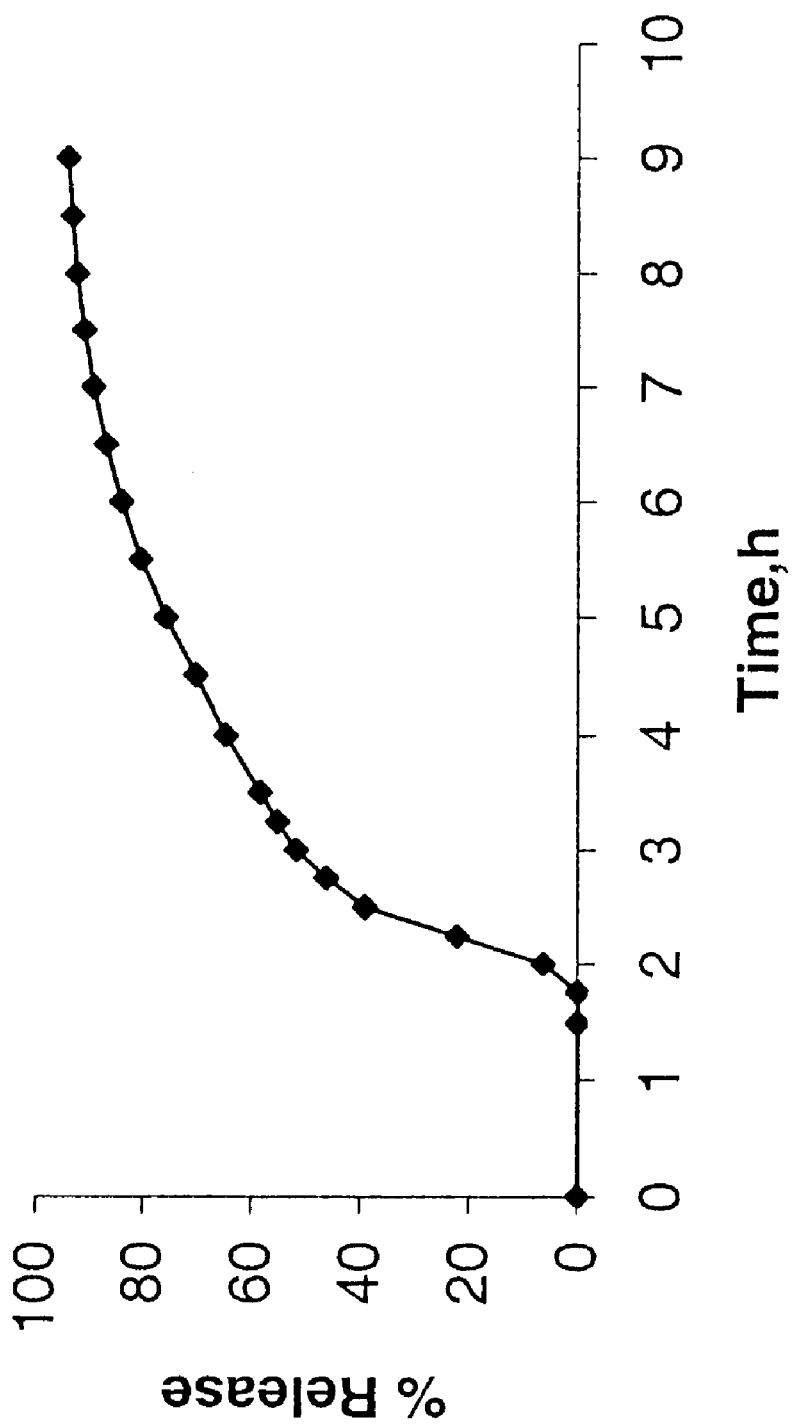

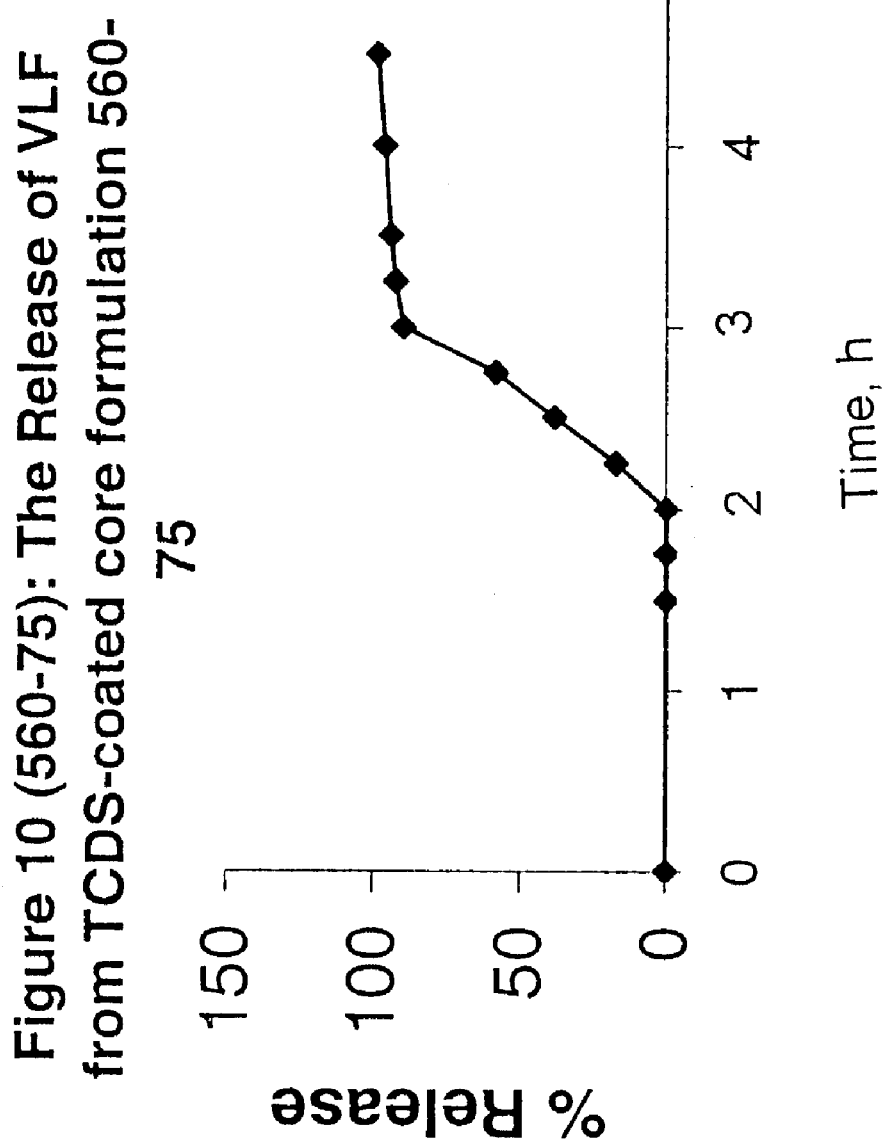

Fig. 11: Mean Venlafaxine Plasma Concentration Time Curve (n=7):
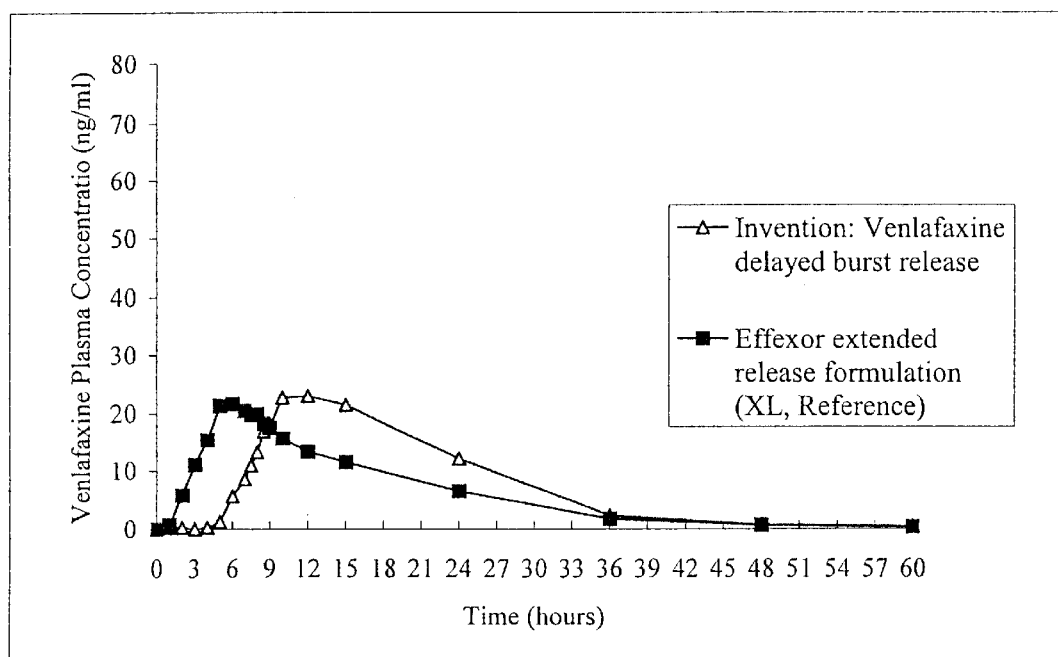

US 6,703,044 B1

VENLAFAXINE FORMULATIONS

FIELD OF THE INVENTION

The present invention relates to a formulation and method for the delayed burst release of venlafaxine.

BACKGROUND OF THE INVENTION

Venlafaxine, 1-[(2-dimethylamino)-1-(4-methoxyphenyl) ethyl] cyclohexanol, is an important drug for the treatment of depression. Venlafaxine and the acid salts thereof are disclosed in U.S. Pat. No. 4,535,186, which is hereby incorporated by reference as if fully set forth herein. Venlafaxine hydrochloride is presently administered to adults in compressed tablet form in doses ranging from 75 to 350 mg/day, in divided doses two or three times a day. Currently, in therapeutic dosing with venlafaxine hydrochloride tablets, rapid dissolution results in a rapid increase in blood plasma levels of the active compound shortly after administration followed by a decrease in blood plasma levels over several hours as the active compound is eliminated or metabolized, until subtherapeutic plasma levels are approached after about twelve hours following administration, thus requiring additional dosing with the drug. With the plural daily dosing regimen, the most common side effect is nausea, experienced by about forty five percent of patients under treatment with venlafaxine hydrochloride. Vomiting also occurs in about seventeen percent of the patients.

U.S. Pat. No. 6,274,171, issued on Aug. 14, 2001, describes one attempted solution to the problem of frequent administration of venlafaxine. The disclosure teaches a formulation of spheroids, which is characterized by an outer film coating over a core which contains venlafaxine, and in which both are placed in a hard gelatine capsule. However, administration of this formulation results in blood concentration levels having a distinct peak 4–8 hours after administration.

Clearly, the ability to provide a more even plateau of blood concentration of venlafaxine, and therefore presumably to reduce the occurrence and/or severity of side effects, or even to eliminate such side effects altogether, as well as decreasing the frequency of administration of venlafaxine, would be desirable. In addition, the location of release of venlafaxine may also be problematic, as the above taught formulations clearly result in release occurring to a significant degree in the small intestine, and possibly also in the stomach. Since one of the most significant side effects of venlafaxine is nausea and/or vomiting, indicating gastric distress, clearly release of this active ingredient should not occur in the stomach and/or small intestine.

In U.S. Pat. Nos. 6,403,120 and 6,419,958 there are described and claimed methods and compositions for providing therapeutic blood plasma concentration of venlafaxine over a twenty-four hour period with diminished incidence of nausea and emesis which comprises administering orally to a patient in need thereof, an extended release formulation as defined in said patents. More specifically one finds in both of said patents a specific description and definition of the term "extended release drug formulations" wherein both of said patents provide the same following description and definition:

"Extended release drug formulations are conventionally produced as compressed tablets by hydrogel tablet technology. To produce these sustained release tablet drug dosage forms, the active ingredient is conventionally compounded with cellulose ethers such as methyl cellulose, ethyl cellulose or hydroxypropylmethylcellulose with or without other excipients and the resulting mixture is pressed into tablets. When the tablets swell upon hydration from moisture in the digestive system, thereby limiting exposure of the active ingredient to moisture. As the cellulose ethers are gradually leached away by moisture, water more deeply penetrates the gel matrix and the active ingredient slowly dissolves and diffuses through the gel, making it available for absorption by the body. An example of such a sustained release dosage form of the analgesic/anti-inflammatory drug etodolac (Lodine®) appears in U.S. Pat. No. 4,966,768. U.S. Pat. No. 4,389,393 discloses sustained release therapeutic compressed solid unit dose forms of an active ingredient plus a carrier base comprised of a high molecular weight hydroxypropylmethylcellulose, methyl cellulose, sodium carboxymethylcelluslose and or other cellulose ether."

Following the above description in said patents there is then presented a further description which states as follows:

"Where the production of tablets is not feasible, it is conventional in the drug industry to prepare encapsulated drug formulations which provide extended or sustained release properties. In this situation, the extended release capsule dosage forms may be formulated by mixing the drug with one or more binding agents to form a uniform mixture which is then moistened with water or a solvent such as ethanol to form an extrudable plastic mass from which small diameter, typically of 1 mm, cylinders of drug/matrix are extruded, broken into appropriate lengths and transformed into spheroids using standard spheronization equipment. The spheroids, after drying, may then be film-coated to retard dissolution. The film-coated spheroids may then be placed in pharmaceutically acceptable capsules, such as starch or gelatin capsules, in the quantity needed to obtain the desired therapeutic effect. Spheroids releasing the drug at different rates may be combined in a capsule to obtain desired release rates and blood levels. U.S. Pat. No. 4,138, 475 discloses a sustained release pharmaceutical composition consisting of a hard gelatin capsule filled with film-coated spheroids comprised of propanolol in admixture with microcrystalline cellulose wherein the film coating is composed of ethyl cellulose, optionally, with hydroxypropylmethylcellulose and/or a plasticizer."

Said patents, having concluded and taught that the preferred solution for obtaining a flattened drug plasma concentration to time profile for extended release of venlafaxine is through use of such extended release drug formulations then specifically described at the top of column three of each of said patents that these formulations are achieved by providing a therapeutically effective amount of venlafaxine hydrochloride in spheroids comprised of venlafaxine, hydrochloride, microcrystalline cellulose and, optionally, hydroxypropylmethylcellulose coated with a mixture of ethyl cellulose and hydroxypropylmethylcellulose.

This is also the solution suggested and taught in U.S. Pat. No. 6,274,171 and in U.S. patent applications 2002/0025339 and U.S. 2001/0055612.

SUMMARY OF THE INVENTION

In contradistinction to the teachings of all of the above mentioned patents and applications that are based on extended release from microspheroids as a function of the structure and coating thereof, it has now been found that a different and better mechanism of long-term dispersion, e.g. for a period of at least 24 hours, of venlafaxine into the blood stream can be achieved by utilizing a formulation which provides for delayed burst release after a period of at least 3 hours after ingestion to provide for dispersion of venlafaxine into the blood stream through the colon over a period extending over at least 24 hours.

Thus, the present invention provides a method for treating a subject with venlafaxine, comprising administering to the subject a formulation having a therapeutically effective amount of venlafaxine or a pharmaceutically acceptable salt thereof, wherein said formulation provides a delayed burst release after at least three hours resulting in dispersion of the active ingredient mainly through the colon into the blood stream as a result of colon absorption over a period of at least 24 hours.

The delivery system of the present invention also advantageously uses the unique continuous absorption characterizing the colon which results in more flat, consistent concentration levels of the drug in blood. Such an absorption, of course, can significantly contribute to reduce the fluctuations in blood drug concentration thus to prevent the side effects which may appear significantly upon using either immediate or conventional controlled release formulations, thereby improving compliance.

The formulation preferably features a core, over which an outer coating is layered. The core is optionally in the form of a tablet, or capsule or any other solid dosage form. The core preferably comprises a burst controlling agent and a disintegrant.

The outer coating preferably features a water insoluble, hydrophobic polymer, in which particles of a water insoluble but hydrophilic material are embedded. These particles preferably form channels upon contact with water or an aqueous medium, thereby enabling the active ingredient to be released upon the burst of the film coat.

In U.S. Pat. No. 5,840,332 there is described and claimed a gastrointenstinal drug delivery system similar to that utilized in the present invention and the relevant teachings of said patent are incorporated herein by reference. It is to be noted however that the diseases contemplated and taught for treatment with such a formulation were selected from the group consisting of colitis, Crohn's disease, irritable bowel syndrome, gastritis, pancreatitis, hypertension, angina, arthritis, rheumatoid, arthritis, asthma, arrythmia, local spasmolytic action, ulceration of the mucosa, diarrhea, constipation, polyps, carcinoma, cysts, infectious disorders, and parasitic disorders, and said patent does not teach nor suggest that said formulation would be effective for the administration of a drug such as venlafaxine for the treatment of depression.

Furthermore, as can be seen from comparative Example 11, table 4 and FIG. 11 presented hereinafter, the formulation of the present invention provides a delayed burst release of venlafaxine resulting in a substantially even plasma concentration level of venlafaxine for a period extending over four hours, and a higher AUC (area under the blood concentration—time curve) when compared with the extended release formulations of venlafaxine presently available on the market and said patent neither teaches nor suggests the surprising characteristics of the venlafaxine formulations of the present invention as demonstrated in said example, table and figure.

Hereinafter, the term "venlafaxine" includes venlafaxine and pharmaceutically acceptable salts thereof, as disclosed for example in U.S. Pat. No. 4,535,186, which was previously incorporated by reference.

The term "hydrophobic" when applied to a film means, besides its common definition, that the film is relatively non-permeable to water and to water-insoluble compounds.

The term "hydrophilic" when applied to a film means, besides its common definition, that the film is relatively permeable to water and to water-soluble compounds.

The term "substantially sustained plateau" of blood concentration levels as used herein refers to a period of time during which the concentration of venlafaxine in the blood exhibits relatively low variability. The substantially sustained plateau preferably occurs for at least about four hours, but more preferably occurs for a longer period of time of at least about eight hours. By "relatively low variability", it is meant that on average, variability is preferably less than about 20% of the blood concentration, and more preferably is less than about 10% of the blood concentration. Similarly, the term "even blood concentration level" also refers to blood concentrations having relatively low variability as previously described.

The dosage levels of the active ingredient venlafaxine could easily be determined by one of ordinary skill in the art. In particular, effective dosages for venlafaxine are well known in the art.

According to the present invention, there is provided a delayed burst formulation as defined, wherein said formulation preferably provides a substantially sustained plateau of blood concentration level of venlafaxine in the subject, wherein said substantially sustained plateau is present for at least four hours.

Preferably the formulation comprises
(a) a core comprising the venlafaxine, wherein said core includes at least one burst controlling agent and a disintegrant, and wherein said core is formed as a compressed tablet; and
(b) an outer coating over said core, said outer coating comprising a water insoluble hydrophobic carrier and water-insoluble but hydrophilic particulate matter, contained in the carrier, that forms channels in the outer coating, upon contact with water or an aqueous medium wherein said channels imbibe liquid and cause said at least one burst controlling agent to burst said coating, thereby enabling the delayed burst release of venlafaxine through these channels after at least three hours followed by dispersion of venlafaxine into the blood stream mainly through the colon over a period extending over at least twenty-four hours.

More preferably, the core is in the form of one of a tablet or a capsule.

Also more preferably, the burst controlling agent comprises a water insoluble polymer for swelling upon contact with liquid, wherein the polymer does not form a hydrogel.

Most preferably, the water insoluble polymer is selected from the group consisting of an insoluble metal salt of a polysaccharide, a heavily cross-linked polysaccharide, pectin, alginic acid, a vegetable gum, water insoluble starch, micro-crystalline cellulose, water insoluble cross-linked peptide, water insoluble cross-linked protein, water insoluble cross-linked gelatin, water insoluble cross-linked hydrolyzed gelatin, water insoluble cross-linked collagen, and carboxymethyl cellulose. Also most preferably, the water insoluble polymer is calcium pectinate or micro-crystalline cellulose.

Preferably, the core further comprises at least one of an absorption enhancer, a binder, a disintegrant, a hardness enhancing agent, and another excipient. More preferably, the binder is selected from the group consisting of starch, PVP (polyvinyl pyrrolidone), low molecular weight HPC (hydroxypropyl cellulose), low molecular weight HPMC (hydroxypropyl methylcellulose), low molecular weight carboxy methyl cellulose, ethylcellulose, gelatin polyethylene oxide, acacia, dextrin, magnesium aluminum silicate, and polymethacrylates. Also more preferably, the hardness enhancing agent is microcrystalline cellulose.

More preferably, the disintegrant is selected from the group consisting of crospovidone (cross-linked PVP) sodium carboxymethyl starch (sodium starch glycolate), cross-linked sodium carboxymethyl cellulose (Croscarmellose), pregelatinized starch (starch 1500), microcrystalline starch, water insoluble starch, calcium carboxymethyl cellulose, magnesium aluminum silicate and a combination thereof.

According to preferred embodiments of the present invention, the core further comprises a buffering agent. Preferably, the buffering agent is selected from the group consisting of an inorganic or organic alkaline salt compound.

Alternatively or additionally, the core further comprises a filler. Preferably, the filler is selected from the group consisting of microcrystalline cellulose, starch, lactitol, lactose, a suitable inorganic calcium salt, sucrose, or a combination thereof.

Also alternatively or additionally, the core further comprises a flow regulating agent. Preferably, the flow regulating agent includes at least one of colloidal silicon dioxide and aluminum silicate.

Preferably, the core further comprises a lubricant. More preferably, the lubricant is selected from the group consisting of stearate salts; stearic acid, talc, sodium stearyl fumarate, and compritol (glycerol behenate), or a combination thereof.

According to other preferred embodiments of the present invention, the water insoluble polymer being used in the film coating composition is relatively rigid. Preferably, the water insoluble polymer is selected from the group consisting of a dimethylaminoethylacrylate/ethylmethacrylate copolymer, the copolymer being based on acrylic and methacrylic acid esters with a low content of quaternary ammonium groups, wherein the molar ratio of the ammonium groups to the remaining neutral (meth)acrylic acid esters is approximately 1:20, the polymer corresponding to USP/NF "Ammonio Methacrylate Copolymer Type A", an ethylmethacrylate/ chlorotrimethylammoniumethyl methacrylate copolymer, the copolymer based on acrylic and methacrylic acid esters with a low content of quaternary ammonium groups wherein the molar ratio of the ammonium groups to the remaining neutral (meth)acrylic acid esters is 1:40, the polymer corresponding to USP/NF "Ammonio Methacrylate Copolymer Type B", a dimethylaminoethylmethacrylate/ methylmethacrylate and butylmethacrylate copolymer, a copolymer based on neutral methacrylic acid esters and dimethylaminoethyl methacrylate esters wherein the polymer is cationic in the presence of acids, an ethylacrylate and methylacrylate/ethylmethacrylate and methyl methylacrylate copolymer, the copolymer being a neutral copolymer based on neutral methacrylic acid and acrylic acid esters, ethylcellulose, shellac, zein, and waxes.

According to still other preferred embodiments of the present invention, the water insoluble particulate matter in the film coating composition is selected from the group consisting of a water insoluble cross-linked polysaccharide, a water insoluble cross-linked protein, a water insoluble cross-linked peptide, water insoluble cross-linked gelatin, water insoluble cross-linked hydrolyzed gelatin, water insoluble cross-linked collagen, a water insoluble cross linked polyacrylic acid, a water insoluble cross-linked cellulose derivatives, water insoluble cross-linked polyvinyl pyrrolidone, micro crystalline cellulose, insoluble starch, micro crystalline starch and a combination thereof.

Preferably, the outer coating further comprises a plasticizer. More preferably, the plasticizer includes at least one of dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof.

Also preferably, the outer coating further comprises a stiffening agent. More preferably, the stiffening agent is cetyl alcohol.

Preferably, the outer coating further comprises at least one of a wetting agent, a suspending agent, and a dispersing agent, or a combination thereof. More preferably, the wetting agent is selected from the group consisting of poloxamer, polyoxyethylene ethers, polyoxyethylene sorbitan fatty acid esters (polysorbates), polyoxymethylene stearate, sodium lauryl sulfate, sorbitan fatty acid esters, benzalkonium chloride, polyethoxylated castor oil, and docusate sodium. Also more preferably, the suspending agent is selected from the group consisting of alginic acid, bentonite, carbomer, carboxymethylcellulose, carboxymethylcellulose calcium, hydroxyethylcellulose, hydroxypropyl cellulose, microcrystalline cellulose, colloidal silicon dioxide, dextrin, gelatin, guar gum, xanthan gum, kaolin, magnesium aluminum silicate, maltitol, medium chain triglycerides, methylcellulose, polyoxyethylene sorbitan fatty acid esters (polysorbates), ppvidone (PVP), propylene glycol alginate, sodium alginate, sorbitan fatty acid esters, and tragacanth. Most preferably, the dispersing agent is selected from the group consisting of poloxamer, polyoxyethylene sorbitan fatty acid esters (polysorbates) and sorbitan fatty acid esters.

According to other preferred embodiments of the present invention, there is provided a method for a treating a subject with venlafaxine, comprising: administering to the subject a formulation having a therapeutically effective amount of venlafaxine or a pharmaceutically acceptable salt thereof, Preferably, the formulation comprises: (a) a core containing the venlafaxine, the core comprising a water insoluble, swellable polymer, and a disintegrant; and (b) a coating comprising a water insoluble, hydrophobic polymer and water-insoluble but hydrophilic particulate matter embedded in the polymer, for forming channels in the outer coating, upon contact with water or an aqueous medium wherein said channels imbibe liquid and cause at least one burst controlling agent to burst the coating, thereby releasing venlafaxine; wherein an amount of the disintegrant and the water insoluble swellable polymer is selected such that the core releases venlafaxine in a manner providing a substantially even blood concentration level of venlafaxine for a period extending over at least about four hours.

According to still another embodiment of the present invention, there is provided a method for providing enhanced bioavailability of venlafaxine in a subject, comprising: administering to the subject a formulation having a therapeutically effective amount of venlafaxine or a pharmaceutically acceptable salt thereof, wherein the formulation provides a substantially sustained plateau of blood concentration level of venlafaxine in the subject, the combination of preferential release in the colon and substantially sustained plateau of blood concentration level resulting in enhanced bioavailability of venlafaxine.

According to another embodiment of the present invention, there is provided a formulation for release of venlafaxine in the colon of a subject, comprising: (a) a core that comprises the venlafaxine, wherein the core includes at least one burst controlling agent and a disintegrant, and wherein the core is formed as a compressed tablet; and (b) an outer coating over the core, the outer coating comprising a water insoluble hydrophobic carrier and water-insoluble but hydrophilic particulate matter, contained in the carrier, for forming channels in the outer coating, upon contact with water or an aqueous medium, wherein said channels imbibe liquid and cause the at least one burst controlling agent to burst the coating, thereby releasing venlafaxine in a delayed burst release after at least three hours followed by dispersion of venlafaxine through the colon into the blood stream over a period extending over at least twenty-four hours.

BRIEF DESCRIPTION OF THE DRAWINGS

The invention is herein described, by way of example only, with reference to the accompanying drawings, wherein:

FIGS. 1–10 are graphic representations of in vitro release profiles of venlafaxine from the formulations as described in the following examples and according to the present invention;

FIG. 11 shows the in vivo release profile of venlafaxine in a bioavailability study.

DESCRIPTION OF THE PREFERRED EMBODIMENTS

The present invention is of a formulation for delayed burst release of an active ingredient mainly in the colon in order to produce a more stable and less variable plateau of the concentration of the active ingredient in the body of the subject. Optionally and more preferably delayed burst release of the active ingredient from the formulation also increases the bioavailability of the active ingredient, although such an increase in bioavailability is not necessary in order to receive the benefit of the formulation according to the present invention. The formulation preferably releases the active ingredient, such as venlafaxine, in the colon.

The core is optionally in the form of a tablet or a capsule or any other solid dosage form. The core preferably features a burst controlling agent. The burst controlling agent is more preferably a water insoluble polymer that swells considerably but preferably does not form a hydrogel or any other type of strong gel. Examples of polymers include but are not limited to, an insoluble metal salt of a polysaccharide such as calcium pectinate or calcium alginate, or a heavily cross-linked polysaccharide such as glutaraldehyde-cross-linked guar gum, pectin, alginic acid, or other vegetable gum, water insoluble starch, micro-crystalline cellulose, water insoluble cross-linked peptide, water insoluble cross-linked protein, water insoluble cross-linked gelatin, water insoluble cross-linked hydrolyzed gelatin, water insoluble cross-linked collagen, and carboxymethyl cellulose. More preferably, the water insoluble polymer at least includes calcium pectinate or microcrystalline cellulose or a combination thereof.

The core preferably also optionally contains one or more of an absorption enhancer, a binder, a disintegrant, another excipient or a combination thereof.

Preferred examples of a binder include but are not limited to starch, PVP (polyvinyl pyrrolidone), low molecular weight HPC (hydroxypropyl cellulose), low molecular weight HPMC (hydroxypropyl methylcellulose), low molecular weight carboxymethyl cellulose, ethylcellulose, gelatin, polyethylene oxide, acacia, dextrin, magnesium aluminum silicate, and polymethacrylates.

Preferred examples of a disintegrant include but are not limited to, Crospovidone (cross-linked PVP), sodium carboxymethyl starch (sodium starch glycolate), cross-linked sodium carboxymethyl cellulose (Croscarmellose), pregelatinized starch (starch 1500), microcrystalline starch, water insoluble starch, calcium carboxymethyl cellulose, magnesium aluminum silicate (Veegum) or a combination thereof.

Optionally and more preferably, the cores also contain a buffering agent such as magnesium stearate, sodium stearate, or any other inorganic or organic alkaline salt compound. Such a buffering agent may optionally at least assist in the maintenance of the pH of the environment of the core, and is more preferably used as needed for the stability of the active ingredient itself.

Other optional ingredients for the core include, but are not limited to, one or more of a filler, a flow regulating agent and a lubricant. Examples of suitable fillers include but are not limited to, microcrystalline cellulose (Avicel™), starch, lactitol, lactose, dibasic calcium phosphate or any other type of suitable inorganic calcium salt and sucrose, or a combination thereof. Examples of suitable lubricants include but are not limited to, stearate salts such as magnesium stearate, calcium stearate, and sodium stearate; stearic acid, talc, sodium stearyl fumarate, and compritol (glycerol behenate), or a combination thereof. Examples of suitable flow regulating agents include but are not limited to, colloidal silicon dioxide and aluminum silicate.

Next, the cores are coated with an outer coating, which preferably includes at least one water insoluble polymer, and optionally and more preferably also includes at least one type of water insoluble but hydrophilic particles or particulate matter embedded in the water insoluble polymer. The coating is preferably designed so that when the formulation enters the gastrointestinal tract, the particles absorb liquid, thus forming channels that interconnect the core with the outer surface of the coating.

The water insoluble polymer is more preferably relatively rigid, and is optionally and more preferably selected from the group consisting of a dimethylaminoethylacrylate/ ethylmethacrylate copolymer, the copolymer being based on acrylic and methacrylic acid esters with a low content of quaternary ammonium groups, wherein the molar ratio of the ammonium groups to the remaining neutral (meth) acrylic acid esters is approximately 1:20, said polymer corresponding to USP/NF "Ammonio Methacrylate Copolymer Type A", an ethylmethacrylate/ chlorotrimethylammoniumethyl methacrylate copolymer, the copolymer based on acrylic and methacrylic acid esters with a low content of quaternary ammonium groups wherein the molar ratio of the ammonium groups to the remaining neutral (meth)acrylic acid esters is 1:40, the polymer corresponding to USP/NF "Ammonio Methacrylate Copolymer Type B", a dimethylaminoethylmethacrylate/ methylmethacrylate and butylmethacrylate copolymer, a copolymer based on neutral methacrylic acid esters and dimethylaminoethyl methacrylate esters wherein the polymer is cationic in the presence of acids, an ethylacrylate and methylacrylate/ethylmethacrylate and methyl methylacrylate copolymer, the copolymer being a neutral copolymer based on neutral methacrylic acid and acrylic acid esters, ethylcellulose, shellac, zein, and waxes.

The water insoluble particulate matter is more preferably selected from the group consisting of a water insoluble cross-linked polysaccharide, a water insoluble cross-linked protein, a water insoluble cross-linked peptide, water insoluble cross-linked gelatin, water insoluble cross-linked hydrolyzed gelatin, water insoluble cross-linked collagen, water insoluble cross linked polyacrylic acid, water insoluble cross-linked cellulose derivatives, water insoluble cross-linked polyvinyl pyrrolidone, micro crystalline cellulose, insoluble starch, micro crystalline starch and a combination thereof.

The outer coating preferably includes at least one plasticizer. Examples of suitable plasticizers include but are not limited to, dibutyl phthalate, diethyl phthalate, dibutyl sebacate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol, polyethylene glycol, propylene glycol and sorbitol. The amount of plasticizer is optionally and more preferably in a range of from about 0 to about 50% weight per weight of the water insoluble polymer in the film coat. In addition or alternatively, a stiffening agent such as cetyl alcohol could optionally be used.

The outer coating may also optionally contain at least one of a wetting agent, suspending agent, surfactant, and dispersing agent, or a combination thereof, in addition to the plasticizer.

Examples of suitable wetting agents include, but are not limited to, poloxamer, polyoxyethylene ethers, polyoxyethylene sorbitan fatty acid esters (polysorbates), polyoxymethylene stearate, sodium lauryl sulfate, sorbitan fatty acid esters, benzalkonium chloride, polyethoxylated castor oil, docusate sodium.

Examples of suitable suspending agents include but are not limited to, alginic acid, bentonite, carbomer, carboxymethylcellulose, carboxymethylcellulose calcium, hydroxyethylcellulose, hydroxypropyl cellulose, microcrystalline cellulose, colloidal silicon dioxide, dextrin, gelatin, guar gum, xanthan gum, kaolin, magnesium aluminum silicate, maltitol, medium chain triglycerides, methylcellulose, polyoxyethylene sorbitan fatty acid esters (polysorbates), polyvinyl pyrrolidone (PVP), propylene glycol alginate, sodium alginate, sorbitan fatty acid esters, and tragacanth.

Examples of suitable surfactants include but are not limited to, anionic surfactants such as docusate sodium and sodium lauryl sulfate; cationic, such as cetrimide; nonionic, such as polyoxyethylene sorbitan fatty acid esters (polysorbates) and sorbitan fatty acid esters.

Examples of suitable dispersing agents include but are not limited to, poloxamer, polyoxyethylene sorbitan fatty acid esters (polysorbates) and sorbitan fatty acid esters.

The content of the wetting agent, surfactant, dispersing agent and suspending agent may optionally be in an amount of from about 0 to about 30% of the weight of the film coat of the formulation. A particularly preferred embodiment of the present invention features crospovidone (cross-linked PVP), calcium pectinate, microcrystalline cellulose, ethylcellulose, polyvinyl pyrrolidone (PVP), colloidal silicon dioxide, and magnesium stearate in the core. The coating for this embodiment preferably features ethyl cellulose, cetyl alcohol, microcrystalline cellulose or calcium pectinate (CaP). Optionally an enteric coating may be applied to these coated cores. Most preferably the enteric coating contains Eudragit L or cellulose acetate phthalate, cellulose acetate succinate, cellulose acetate succinate phthalate, hydroxypropyl methyl cellulose acetate succinate. This embodiment is particularly preferred for the administration of venlafaxine.

As described in greater detail below, other pharmaceutically acceptable excipients may also be used in the formulations of the present invention.

The combination of the selected materials for the core matrix and outer layer, and the relative concentrations thereof, as well as the thickness of the core matrix and outer layer, determine both the lag time, which is the time, post administration, when the release starts, as well as the rate of release of the drug.

As previously described, release of the drug is optionally possible through any type of mechanism, including but not limited to, disintegration, burst release, diffusion, permeation (release through pores or channels), or erosion, or a combination thereof. The type of mechanism may be destructive to the outer layer or non-destructive; the continuity and/or structure of the outer layer may be maintained, or altered and/or destroyed. Without wishing to be limited to a single mechanism, for the preferred embodiments of the present invention, both the outer layer and the core preferably permit the drug to be released through some type of destructive process, including but not limited to, burst release, erosion and disintegration of the core, or a combination thereof. However, a mixture of mechanisms is also possible.

Burst release is the preferred mechanism for release of the active ingredient. Without wishing to be limited by a single hypothesis, the preferred embodiment of the formulation according to the present invention preferably features a core which contains a swellable material, covered by a coating which includes a water insoluble hydrophobic carrier. The coating also includes water insoluble but hydrophilic particulate matter. When this particulate matter comes into contact with water or an aqueous medium, the particulate matter imbibes water and swells, thereby forming channels which enable the water to enter the core. The swellable material in the core then swells and bursts the coating, after which the core more preferably disintegrates slowly or otherwise releases the active ingredient.

EXAMPLES

Examples 1–10

These examples are of illustrative implementations of the formulation according to the present invention with venlafaxine. It should be noted that all examples given herein use venlafaxine hydrochloride, referred to herein as "venlafaxine" for the purpose of brevity and without any intention of being limiting. The formulations were tested in vitro to determine the release profile, as described in greater detail below.

TABLE 1

Different formulations of the core containing VLF, and CUP-containing TCDS coating

| Tablets | 560-8 | | 560-11 | | 560-15 | |
|---|---|---|---|---|---|---|
| content | Mg/tab | % | mg/tab | % | mg/tab | % |
| Core: | | | | | | |
| Venlafaxine | 85 | 26.8 | 85 | 26.6 | 85 | 26.6 |
| Crospovidone | 41.5 | 13.0 | 41.3 | 12.9 | 39 | 12.2 |
| Ca Pectinate | | | | | 47 | 14.7 |
| Microcrystalline cellulose | 166 | 52.2 | 169.3 | 52.9 | 128 | 40 |
| Ethylcellulose | 15.9 | 5 | 16.0 | 5.0 | 13 | 4.0 |

TABLE 1-continued

Different formulations of the core containing VLF, and CUP-containing TCDS coating

|  |  |  |  |  |  |  |
|---|---|---|---|---|---|---|
| Polyvinylpyrrolidone |  |  |  |  |  |  |
| Colloidal Silicon Dioxide | 6.0 | 1.9 | 6.4 | 2.0 | 6 | 1.9 |
| Magnesium Stearate | 3.1 | 1.0 | 2.0 | 0.6 | 2 | 0.6 |
| Total weight uncoated tablet | 317.5 | 100 | 320 | 100 | 320 | 100 |
| CaP Coating: | 560-9 | | 560-12 | | 560-16 | |
| CaP Ethylcellulose | | | 47.6% | | | |
| Cetyl Alcohol | | | 4.8% | | | |
| CaP | | | 47.6% | | | |

The in vitro release of venlafaxine from the above-referenced formulations was determined as follows. Six venlafaxine formulation tablets were inserted into individual dissolution cells, each of which contain 450 ml HCl (0.1 M). After two hours, the dissolution medium was changed by adding 450 ml of 100 mM potassium dihydrogen phosphate and adjusting the pH to pH=6.8. The sample was stirred with a VanKel paddle stirrer (Van Kel Inc., USA). Samples were automatically drawn from each dissolution cell to test tubes at various time points (every half-hour from 2.5 hours to 7 hours after the pH was adjusted to pH=6.8), and were analyzed by a UV (ultraviolet) light detection and analysis device. A VK 8000 autosampler was used to analyze the samples (Van Kel Inc., USA). The amount of venlafaxine hydrochloride was measured at 227 nm light, and the amount of drug released was calculated according to a standard set of calculations that are known in the art.

Example 1 (560-9)

The cores were manufactured by dry mixing. Venlafaxine HCl (34 g) was mixed with colloidal silicon dioxide (2.4 g). The obtained mixture was sieved by sieve 600 microns and blended with crospovidone (16.6 g), microcrystalline cellulose (66.4 g) and polyvinyl pyrrolidone (6 g). Magnesium stearate (0.12 g) was passed through mechanical sieve equipped with 600 micron screen into the mixture and blended.

Tabletting

The tablets' blend was compressed with WICK single punch tabletting press equipped with suitable punches for providing sufficient active material and hardness sufficient for subsequent coating.

TCDS Coating

The formed cores were then coated with a TCDS coating containing calcium pectinate. (ingredients and concentrations given in the tables above), The coating process was prepared and performed as follows. A weighed quantity of ethyl cellulose 20 (0.30 kg) was dissolved in ethanol (6.06 kg) to obtain clear solution, to which a weighed quantity of plasticizer (cetyl alcohol-0.03 kg) was added and mixed with mechanical stirrer to complete dissolution. Microcrystalline Cellulose (0.3 kg) was added and stirred to obtain a homogeneous suspension, which was stirred during the whole coating process.

The TCDS coating was performed in a perforated pan coater, with an applied spraying pressure of 2.5 Bar. The suspension was coated until the weight of the coating was about 40–50 mg. The tablets were dried.

FIG. 1 shows the results for the release of venlafaxine from formulation 560-9. As shown, release is delayed until 3 hours after being placed in the more basic medium, which is sufficient to demonstrate that venlafaxine would be preferentially released at the colon.

Example 2 (560-11)

Venlafaxine HCl(50 g) was mixed with disintegrator (cross-linked polyvinyl pyrrolidone-2.5 g) and binder polyvinyl pyrrolidone and the granulation solution (water purified) was added. The blend was mixed until sufficient consistency was achieved. The granulated blend was dried.

The dried granulation blend was milled to obtain the desired particle size distribution of the final granulation blend.

Next, the process of blending was performed for the second part of the core. Colloidal silicon dioxide (3.2 g) was mixed with an additional amount of crospovidone (18.5 g ) and sieved by a mechanical sieve equipped with a 600 micron screen into the previously obtained granulation blend. The obtained mixture was blended. Microcrystalline cellulose (84.7 g) was added into the mixture and the entirety was blended.

Magnesium stearate (1.0), which serves as lubricant, was passed through a mechanical sieve equipped with a 600 micron screen into the mixture and blended for 2 minutes. This last process formed the tabletting mixture.

The tabletting mixture was then compressed with a WICK single punch tabletting press equipped with suitable punches, as previously described.

The formed cores were then coated with TCDS coating that was prepared as follows. A weighed quantity of Ethylcellulose 20 (10 g) was dissolved in ethanol (200 g) to obtain a clear solution, to which a weighed quantity of plasticizer (cetyl alcohol-1.0 g) was added and mixed with the mechanical stirrer to complete dissolution. Sieved calcium pectinate (10 g) was added and stirred to obtain a homogeneous suspension, which was stirred during the whole coating process.

The coating was performed in a perforated pan coater, with the temperature of the incoming air kept to 28–32° C. and with an applied spraying pressure of 0.4 Bar. The tablets were dried in the oven at 35° C. overnight.

FIG. 2 shows the results for the release of venlafaxine from formulation 560-12. As shown, release is sufficiently delayed after being placed in the more basic medium to demonstrate that venlafaxine would be preferentially released at the colon.

Example 3 (560-15)

Venlafaxine HCl (42.5 g) was mixed with calcium pectinate (023.5 g) and disintegrator (cross-linked polyvinyl pyrrolidone-3.5 g), and the granulation solution (polyvinyl pyrrolidone 3 g dissolved in 30 g Ethanol) was added. The blend was mixed until sufficient consistency was achieved. The granulated blend was dried.

The dried granulation blend was milled to obtain the desired particle size distribution of the final granulation blend.

Next, the process of blending was performed for the second part of the core. Colloidal silicon dioxide (2.4 g) was mixed with granulate and sieved by a mechanical sieve equipped with a 600 micron screen. The obtained mixture was blended. Microcrystalline cellulose(51.2 g), cross-linked polyvinyl pyrrolidone (12.8g) and polyvinyl pyrrolidone-(2.8 g) were added into the mixture and the entirety was blended.

Magnesium stearate(0.8 g), which serves as lubricant, was passed through a mechanical sieve equipped with a 600 micron screen into the mixture and blended. This last process formed the tabletting mixture.

The tabletting mixture was then compressed with a WICK single punch tabletting press equipped with suitable punches, as previously described.

The TCDS coating was prepared and added as previously described in Examples 1 and 2, containing calcium pectinate.

FIG. 3 shows the results for the release of venlafaxine from formulation 560-16. As shown, release is sufficiently delayed after being placed in the more basic medium to demonstrate that venlafaxine would be preferentially released at the colon.

polyvinylpyrrolidone-2.5 g ) and the granulation solution (1.1 g Ethocel 7 in 15 g Ethanol)) was added. The blend was mixed until sufficient consistency was achieved. The granulated blend was dried. The remainder of the process was performed as previously described.

The coating again contained microcrystalline cellulose, to form formulation 560-24/B. Again, as shown in FIG. 5 release is sufficiently delayed after being placed in the more basic medium to demonstrate that venlafaxine would be preferentially released at the colon.

The formulation 560-23 was performed as for 560-22 but polyvinyl pyrrolidone was used as a binder instead of ethyl cellulose. The coating again contained microcrystalline cellulose, to form formulation 560-24/C. FIG. 6 shows the release profile of the formulation 560-24C. As shown, the release is sufficiently delayed after being placed in the more basic medium to demonstrate that venlafaxine would be preferentially released at the colon.

Example 6 (241201)

Granulation

Venlafaxine HCl (1.697 kg) was granulated with binder (Povidone K-30-0.054 kg) and disintegrant (cross-linked

TABLE 2

Different formulations of the core containing VLF, and microcristalline cellulose-containing TCDS coating

| Tablets content | 560-21 | | 560-22 | | 560-23 | | 241201 | |
|---|---|---|---|---|---|---|---|---|
| | mg/tab | % | mg/tab | % | mg/tab | % | mg/tab | % |
| Core: | | | | | | | | |
| Venlafaxine | 85 | 26.6 | 85 | 26.6 | 85 | 26.6 | 84.85 | 26.52 |
| Crospovidone | 41.3 | 12.9 | 43.0 | 13.4 | 39 | 12.2 | 41.65 | 13.02 |
| Ca Pectinate | | | 47 | 14.7 | 47 | 14.7 | | |
| Microcrystalline cellulose (Avicel PH 102) | 169.3 | 52.9 | 134 | 41.9 | 128 | 40 | 170 | 53.12 |
| Ethylcellulose | | | 3 | 0.9 | | | | |
| Polyvinylpyrrolidone | 16.0 | 5 | | | 13 | 4.0 | 15.1 | 4.72 |
| Colloidal Silicon Dioxide | 6.4 | 2.0 | 6.0 | 1.9 | 6 | 1.9 | 6.4 | 2.0 |
| Magnesium Stearate | 2.0 | 0.6 | 2.0 | 0.6 | 2 | 0.6 | 2.0 | 0.62 |
| Total weight uncoated tablet | 320 | 100 | 320 | 100 | 320 | 100 | 320 | 100 |
| Coating: | 560-24/A | | 560-24/B | | 560-24/C | | 241201 | |
| Ethylcellulose | | | | | 47.6% | | | |
| Cetyl Alcohol | | | | | 4.8% | | | |
| Microcrystalline cellulose (Avicel PH 101) | | | | | 47.6% | | | |

Venlafaxine HCl(50 g) was mixed with disintegrator (cross-linked polyvinylpyrrolidone-2.5 g) and binder-polyvinyl pyrrolidone (1 g) and the granulation solution (water purified) was added. Colloidal silicon dioxide (0.6 g) was added for improvement porosity of granulate. The blend was mixed until sufficient consistency was achieved. The granulated blend was dried.

The remainder of the process was performed as previously described, except that the coating contained microcrystalline cellulose, to form formulation 560-24/A. As shown (FIG. 4), release is sufficiently delayed after being placed in the more basic medium to demonstrate that venlafaxine would be preferentially released at the colon.

Example 5 (560-22, 560-23)

Venlafaxine HCl(30.3 g) was mixed with calcium pectinate (16.8 g), and disintegrant (cross-linked polyvinyl pyrrolidone-0.093 kg), and water purified (0.275 kg) was added.

The remainder of the process was performed as previously described. FIG. 7 shows the results of the release profile for 241201. FIG. 8 shows the results of the in vitro release for the formulation 241201E, which has a TCDS coating that contains microcrystalline cellulose, over which an enteric coat has been added. As shown, release is sufficiently delayed after being placed in the more basic medium to demonstrate that venlafaxine would be preferentially released at the colon.

Example 7 (180502)

Granulation

Venlafaxine HCl (0.848 kg) was granulated with calcium pectinate (0.700 kg) and disintegrant (cross-linked polyvinyl pyrrolidone-0.070 kg). Binder solution (Povidone K-30-0.0085 kg)and purified water (0.350 kg) was added.

The remainder of the process was performed as previously described. FIG. 9 shows the results, for the formulation 180502, which has a TCDS coating that contains microcrystalline cellulose. This formulation shows a slightly withdrawn pre-dose and at: 1, 2, 3, 4, 5, 6, 7, 7.5, 8, 8.5, 9, 10, 12, 15, 24, 36, 48 and 60 hours post-dose.

Plasma concentrations of venlafaxine were determined using an HPLC analytical method with UV detection.

TABLE 3

| | Venlafaxine Formulations | | | | | | | |
|---|---|---|---|---|---|---|---|---|
| | 240402 | | 180502 | | 560-74 | | 560-78 | |
| Tablets content | mg/tab | % | mg/tab | % | mg/tab | % | mg/tab | % |
| Core: | | | | | | | | |
| Venlafaxine | 84.85 | 26.5 | 84.85 | 26.5 | 135.8 | 22.6 | 67.9 | 22.6 |
| Crospovidone | 39 | 12.2 | 39 | 12.2 | 77.4 | 12.9 | 39 | 13.0 |
| Ca Pectinate | 70 | 21.9 | 70 | 21.9 | | | | |
| Sodium Lauril Sulphate | | | | | | | 5 | 1.7 |
| Microcrystalline cellulose (Avicel PH 102) | 106.15 | 33.2 | 106.15 | 33.2 | 343.4 | 57.2 | 168 | 56.0 |
| Polyvinylpyrrolidone | 12 | 3.7 | 12 | 3.7 | 27.6 | 4.6 | 12.2 | 4.1 |
| Colloidal Silicon Dioxide | 6.1 | 1.9 | 6.1 | 1.9 | 12.0 | 2 | 6.0 | 2.0 |
| Magnesium Stearate | 1.9 | 0.6 | 1.9 | 0.6 | 3.8 | 0.6 | 1.9 | 0.6 |
| Total weight uncoated tablet | 320 | 100 | 320 | 100 | 600 | 100 | 300 | 100 |
| TCDS Coating: | 240402 | | 180502 | | 560-75/A | | 560-79 | |
| Ethylcellulose | | | 47.6% | | | | 47.6% | |
| Cetyl Alcohol | | | 4.8% | | | | 4.8% | |
| Microcrystalline cellulose (Avicel PH 102) | | | 47.6% | | | | 47.6% | |
| Enterocoating: | | | | | | | | |
| Eudragit L30 D55 | | | 76.8% | | | | | |
| Triethylcitrate | | | 15.5% | | | | | |
| Talc | | | 7.7% | | | | | | delayed release, sufficient to show that release would preferentially occur in the colon.

Example 9: (180502E)

The process of example 8 was repeated with additional enterocoating after TCDS coating.

Example 10: (560-74)

Venlafaxine HCl (0.5 kg) was granulated with binder (Povidone K-30-0.0162 kg), and disintegrant (cross-linked polyvinyl pyrrolidone—0.0274 kg) and purified water (0.081 kg).

The remainder of the process was performed as previously described. FIG. 10 shows the in vitro release of venlafaxine of the formulation 560-74, which has a TCDS coating that contains microcrystalline cellulose. This formulation shows a delayed release, sufficient to show that release would preferentially occur in the colon.

Example 11: Pilot Study of Bioavailability (Venlafaxine)

A pilot study was undertaken to investigate the Pharmacokinetic profile of the test formulation 241201 for Venlafaxine DR 75 mg tablets, which were prepared as previously described above in a comparative study as compared with Effexor XL (extended release formulation).

The formulation according to the present invention was administered to fasting volunteers and blood samples were The presented values for all pharmacokinetic parameters are mean ±SD and (range). These values were calculated for eight volunteers (n=7). The extent of absorption as reflected by the AUC values and the rate of absorption as reflected by the Cmax values as well as the rate of absorption as reflected by the Tmax values for volunteers using venlafaxine according to the present invention and Effexor XL are presented in Table 4 hereinafter FIG. 11 shows the blood concentration values for the venlafaxine DR formulation according to the present invention vs. Effexor ER after administration.

TABLE 4

PHARMACOKINETIC PARAMETERS
Venlafaxine Test versus Efexor Reference

| | AUC (ng × hour/ml) | Cmax (ng/ml) | Tmax (hours) |
|---|---|---|---|
| VENLAFAXINE DR 75 mg (DEXCEL) B.N. 241201 | 408.66 ± 300.80 (63.33 ; 957.43) | 30.26 ± 16.90 (10.24 ; 57.02) | 11.79 ± 2.51 (8.50 ; 15.00) |
| EFFEXOR XL 75 mg (WYETH) B.N. A990612A | 338.39 ± 244.45 (21.73 ; 780.94) | 22.24 ± 12.65 (5.63 ; 44.38) | 6.00 ± 0.82 (5.00 ; 7.00) |
| RATIO* (90% ANOVA C.I.) | 1.30 (0.94 ; 1.81) | 1.38 (0.99 ; 1.92) | |

TABLE 4-continued

PHARMACOKINETIC PARAMETERS
Venlafaxine Test versus Efexor Reference

|  | AUC (ng × hour/ml) | Cmax (ng/ml) | Tmax (hours) |
|---|---|---|---|
| DIFFERENCE** |  |  | 5.79 ± 1.78 |
| (RANGE) |  |  | (3.50 ; 8.00) |

The presented values for all pharmacokinetic parameters are mean ± SD and (range).
*The presented ratios are geometric means of the individual ratios between test and reference parameters. Parametric estimators and Parametric Confidence Intervals, based on the linear model with logarithmic transformation, are brought.
**The presented difference are the mean results and the range of Tmax.

As stated hereinbefore and as can be seen from FIG. 11 and Table 4, surprisingly the delayed burst release formulations of venlafaxine according to the present invention result in a more even plasma concentration over a longer period of time as well as a greater bio-availability, as reflected by the greater AUC, when compared with the extended release formulation of venlafaxine presently available on the market.

These improved characteristics of the present formulations enable the administration of lower dosages and the consequent reduction of undesirable side effects.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for treating a subject with venlafaxine, comprising:
   administering to the subject a formulation having a therapeutically effective amount of venlafaxine or a pharmaceutically acceptable salt thereof, wherein said formulation provides a delayed burst release after at least three hours resulting in dispersion mainly through the colon of the active ingredient into the blood stream as a result of colon absorption over a period of at least 24 hours.

2. A method for providing enhanced bioavailability of venlafaxine in a subject, comprising: administering to the subject a formulation having a therapeutically effective amount of venlafaxine or a pharmaceutically acceptable salt thereof, wherein said formulation provides delayed burst release of venlafaxine after at least three hours followed by dispersion of venlafaxine into the blood stream mainly through the colon over a period extending over at least twenty-four hours and wherein said release in the colon results in enhanced bioavailability of venlafaxine.

3. The method of claim 1, wherein said formulation comprises:
   (a) a core that comprises an effective amount of venlafaxine, wherein said core includes at least one burst controlling agent and a disintegrant, and wherein said core is formed as a compressed tablet; and
   (b) an outer coating over said core, said outer coating comprising a water insoluble hydrophobic carrier and water-insoluble but hydrophilic particulate matter, contained in the carrier, that forms channels in said outer coating upon contact with the colon medium, wherein said channels imbibe liquid and cause said at least one burst controlling agent to burst said coating, thereby enabling the delayed burst release of venlafaxine after at leas t three hours followed by dispersion of venlafaxine into the blood stream mainly through the colon over a period extending over at least twenty-four hours.

4. The method of claim 3 wherein said core is in the form of a tablet or a capsule containing the same.

5. The method of claim 3, wherein said burst controlling agent comprises a water insoluble polymer for swelling upon contact with liquid, wherein said polymer does not form a hydrogel.

6. The method of claim 5, wherein said water insoluble polymer is selected from the group consisting of an insoluble metal salt of a polysaccharide, a heavily cross-linked polysaccharide, pectin, alginic acid, a vegetable gum, water insoluble starch, micro-crystalline cellulose, water insoluble cross-linked peptide, water insoluble cross-linked protein, water insoluble cross-linked gelatin, water insoluble cross-linked hydrolyzed gelatin, water insoluble cross-linked Collagen, and carboxymethyl cellulose.

7. The method of claim 6, wherein said water insoluble polymer is calcium pectinate.

8. The method of claim 3, wherein said core further comprises at least one of an absorption enhancer, a binder, a disintegrant, a hardness enhancing agent, and another excipient.

9. The method of claim 8, wherein said binder is selected from the group consisting of starch, PVP (polyvinyl pyrrolidone), low molecular weight HPC (hydroxypropyl cellulose), low molecular weight HPMC (hydroxypropyl methylcellulose), low molecular weight of carboxy methyl cellulose, ethylcellulose, gelatin polyethylene oxide, acacia, dextrin, magnesium aluminum silicate, and polymethacrylates.

10. The method of claim 8, wherein said hardness enhancing agent is microcrystalline cellulose.

11. The method of claim 8, wherein said disintegrant is selected from the group consisting of crospovidone (cross-linked PVP) sodium carboxymethyl starch (sodium starch glycolate), cross-linked sodium carboxymethyl cellulose (Croscarmellose), pregelatinized starch (starch 1500), microcrystalline starch, water insoluble starch, calcium carboxymethyl cellulose, magnesium aluminum silicate and a combination thereof.

12. The method of claim 10, wherein said core further comprises a buffering agent.

13. The method of claim 12, wherein said buffering agent is selected from the group consisting of an inorganic or organic alkaline salt compound.

14. The method of claim 8, wherein said core further comprises a filler.

15. The method of claim 14, wherein said filler is selected from the group consisting of microcrystalline cellulose, starch, lactitol, lactose, a suitable inorganic calcium salt, sucrose, or a combination thereof.

16. The method of claim 8, wherein said core further comprises a flow regulating agent.

17. The method of claim 16, wherein said f low regulating agent includes at least one of colloidal silicon dioxide and aluminum silicate.

18. The method of claim 8, wherein said core further comprises a lubricant.

19. The method of claim 18, wherein said lubricant is selected from the group consisting of stearate salts; stearic acid, talc, sodium stearyl fumarate, and compritol (glycerol behenate), or a combination thereof.

20. The method of claim 3, wherein said water insoluble polymer is relatively rigid.

21. The method of claim 20, wherein said water insoluble polymer is selected from the group consisting of a dimethylaminoethylacrylate/ethylmethacylate copolymer, the copolymer being based on acrylic and methacrylic acid esters with a low content of quaternary ammonium groups, wherein the molar ratio of the ammonium groups to the remaining neutral (meth)acrylic acid esters is approximately 1:20, said polymer corresponding to USP/NF "Ammonio Methacrylate Copolymer Type A", an ethylmethacrylate/chlorotrimethylammoniumethyl methacrylate copolymer, the copolymer based on acrylic and methacrylic acid esters with a low content of quaternary ammonium groups wherein the molar ratio of the ammonium groups to the remaining neutral (meth)acrylic acid esters is 1:40, the polymer corresponding to USP/NF "Ammonio Methacrylate Copolymer Type B", dimethylaminoethylmethacrylate/methylmethacrylate and butylmethacrylate copolymer, a copolymer based on neutral methacrylic acid esters and dimethylaminoethyl methacrylate esters wherein the polymer is cationic in the presence of acids, an ethylacrylate and methylacrylate/ethylmethacrylate and methyl methylacrylate copolymer, the copolymer being a neutral copolymer based on neutral methacrylic acid and acrylic acid esters, ethylcellulose, shellac, zein, and waxes.

22. The method of claim 3, wherein said water insoluble particulate matter is selected from the group consisting of a water insoluble cross-linked polysaccharide, a water insoluble cross-linked protein, a water insoluble cross-linked peptide, water insoluble cross-linked gelatin, water insoluble cross-linked hydrolyzed gelatin, water insoluble cross-linked collagen, a water insoluble cross linked polyacrylic acid, a water insoluble cross-linked cellulose derivatives, water insoluble cross-linked polyvinyl pyrrolidone, micro crystalline cellulose, insoluble starch, micro crystalline starch and a combination thereof.

23. The method of claim 3, wherein said outer coating further comprises a plasticizer.

24. The method of claim 23, wherein said plasticizer includes at least one of dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof.

25. The method of claim 3, wherein said outer coating further comprises a stiffening agent.

26. The method of claim 25 wherein said stiffening agent is cetyl alcohol.

27. The method of claim 3, wherein said outer coating further comprises at least one of a wetting agent, a suspending agent, and a dispersing agent, or a combination thereof.

28. The method of claim 27, wherein said wetting agent is selected from the group consisting of poloxamer, polyoxyethylene ethers, polyoxyethylene sorbitan fatty acid esters (polysorbates), polyoxymethylene stearate, sodium lauryl sulfate, sorbitan fatty acid esters, benzalkonium chloride, polyethoxylated castor oil, and docusate sodium.

29. The method of claim 27, wherein said suspending agent is selected from the group consisting of alginic acid, bentonite, carbomer, carboxymethylcellulose, carboxymethylcellulose calcium, hydroxyethylcellulose, hydroxypropyl cellulose, microcrystalline cellulose, colloidal silicon dioxide, dextrin, gelatin, guar gum, xanthan gum, kaolin, magnesium aluminum silicate, maltitol, medium chain triglycerides, methylcellulose, polyoxyethylene sorbitan fatty acid esters (polysorbates), povidone (PVP), propylene glycol alginate, sodium alginate, sorbitan fatty acid esters, and tragacanth.

30. The method of claim 27, wherein said dispersing agent is selected from the group consisting of poloxamer, polyoxyethylene sorbitan fatty acid esters (polysorbates) and sorbitan fatty acid esters.

31. The method of claim 2, wherein said dispersion into the blood stream results in a substantially sustained plateau for a period of at least 4 hours, said plateau having a variability between blood concentrations of less than about 20%.

32. The method of claim 31, wherein said variability is less than about 10%.

33. The method of claim 1, wherein said formulation comprises:
(a) a core that comprises an effective amount of venlafaxine, said core comprising a water insoluble, non-hydrogel forming swellable polymer, and a disintegrant; and
(b) a coating comprising a water insoluble, hydrophobic polymer and water-insoluble but hydrophilic particulate matter embedded in said polymer, that forms channels in the outer coating, wherein said channels imbibe liquid and cause said at least one burst controlling agent to burst said coating, thereby releasing venlafaxine;
wherein an amount of said disintegrant and said water insoluble swellable polymer is selected such that said core releases venlafaxine in a manner providing an even blood concentration level of venlafaxine for a period extending over at least about four hours.

34. A method for treating a subject with venlafaxine, comprising:
administering to the subject a formulation having a therapeutically effective amount of venlafaxine or a pharmaceutically acceptable salt thereof, said formulation comprising a compressed tablet that comprises said venlafaxine, wherein said compressed tablet contains at least one lubricant, and wherein said formulation provides delayed burst release of venlafaxine after at least three hours followed by dispersion of venlafaxine into the blood stream through the colon over a period extending over at least twenty-four hours.

35. A formulation for release of venlafaxine mainly in the colon of a subject, comprising:
(a) a core that comprises an effective amount of venlafaxine, wherein said core contains at least one burst controlling agent and a disintegrant, and wherein said core is formed as a compressed tablet; and
(b) an outer coating over said core, said outer coating comprising a water insoluble hydrophobic carrier and water-insoluble but hydrophilic particulate matter, contained in the carrier, that forms channels in said outer coating material upon contact with the colon medium, wherein said channels imbibe liquid and cause said at least one burst controlling agent to burst said coating, thereby providing delayed burst release of venlafaxine after at least three hours followed by dispersion of venlafaxine into the blood stream mainly through the colon over a period extending over at least twenty-four hours.

36. The formulation of claim 35, wherein said disintegrant is selected from the group consisting of crospovidone (cross-linked PVP), sodium carboxymethyl starch (sodium starch glycolate), cross-linked sodium carboxymethyl cellulose (Croscarmellose), pregelatinized starch (starch 1500), microcrystalline starch, water insoluble starch, calcium carboxymethyl cellulose, magnesium aluminum silicate (Veegum) or a combination thereof.

37. The formulation o f claim 36, wherein said burst controlling agent comprises a water insoluble polymer for swelling upon contact with liquid, wherein said polymer does not form a hydrogel.

38. The formulation of claim 36, wherein said water insoluble polymer is selected from the group consisting of an insoluble metal salt of a polysaccharide, a heavily cross-linked polysaccharide, pectin, alginic acid, another type of vegetable gum, water insoluble starch, micro-crystalline cellulose, water insoluble cross-linked peptide, water insoluble cross-linked protein, water insoluble cross-linked gelatin, water insoluble cross-linked hydrolyzed gelatin, water insoluble cross-linked collagen, and carboxymethyl cellulose.

39. The formulation of claim 37, wherein said water insoluble polymer is calcium pectinate.

40. The formulation of claim 37, wherein said water insoluble polymer is micro-crystalline cellulose.

41. The formulation of claim 35, wherein said core further comprises at least one of an absorption enhancer, a binder, and another excipient.

42. The formulation of claim 41, wherein said binder is selected from the group consisting of starch, PVP (polyvinyl pyrrolidone), low molecular weight HPC (hydroxypropyl cellulose), low molecular weight HPMC (hydroxypropyl methylcellulose), low molecular weight of carboxy methyl cellulose, ethylcellulose, gelatin polyethylene oxide, acacia, dextrin, magnesium aluminum silicate, and polymethacrylates.

43. The formulation of claim 41, wherein said core further comprises a buffering agent.

44. The formulation of claim 42, wherein said buffering agent is selected from the group consisting of an inorganic or organic alkaline salt compound.

45. The formulation of claim 35, wherein said core further comprises a filler.

46. The formulation of claim 45, wherein said filler is selected from the group consisting of microcrystalline cellulose, starch, lactitol, lactose, a suitable inorganic calcium salt, sucrose, or a combination thereof.

47. The formulation of claim 35, wherein said core further comprises a flow regulating agent.

48. The formulation of claim 46, wherein said flow regulating agent includes at least one of colloidal silicon dioxide and aluminum silicate.

49. The formulation of claim 35, wherein said core further comprises a lubricant.

50. The formulation of claim 49, wherein said lubricant is selected from the group consisting of stearate salts; stearic acid, talc, sodium stearyl fumarate, and compritol (glycerol behenate), or a combination thereof.

51. The formulation of claim 35, wherein said water insoluble polymer is relatively rigid.

52. The formulation of claim 51, wherein said water insoluble polymer is selected from the group consisting of a dimethylaminoethylacrylate/ethylmethacrylate copolymer, the copolymer being based on acrylic and methacrylic acid esters with a low content of quaternary ammonium groups, wherein the molar ratio of the ammonium groups to the remaining neutral (meth)acrylic acid esters is approximately 1:20, said polymer corresponding to USP/NF "Ammonio Methacrylate Copolymer Type A", an ethylmethacrylate/chlorotrimethylammoniumethyl methacrylate copolymer, the copolymer based on acrylic and methacrylic acid esters with a low content of quaternary ammonium groups wherein the molar ratio of the ammonium groups to the remaining neutral (meth)acrylic acid esters is 1:40, the polymer corresponding to USP/NF "Ammonio Methacrylate Copolymer Type B", a dimethylaminoethylmethacrylate/methylmethacrylate and butylmethacrylate copolymer, a copolymer based on neutral methacrylic acid esters and dimethylaminoethyl methacrylate esters wherein the polymer is cationic in the presence of acids, an ethylacrylate and methylacrylate/ethylmethacrylate and methyl methylacrylate copolymer, the copolymer being a neutral copolymer based on neutral methacrylic acid and acrylic acid esters, ethylcellulose, shellac, zein, and waxes.

53. The formulation of claim 35, wherein said water insoluble particulate matter is selected from the group consisting of a water insoluble cross-linked polysaccharide, a water insoluble cross-linked protein, a water insoluble cross-linked peptide, water insoluble cross-linked gelatin, water insoluble cross-linked hydrolyzed gelatin, water insoluble cross-linked collagen, a water insoluble cross linked polyacrylic acid, a water insoluble cross-linked cellulose derivatives, water insoluble cross-linked polyvinyl pyrrolidone, micro crystalline cellulose, insoluble starch, micro crystalline starch and a combination thereof.

54. The formulation of claim 35, wherein said outer coating further comprises a plasticizer.

55. The formulation of claim 54, wherein said plasticizer includes at least one of dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof.

56. The formulation of claim 35, wherein said outer coating further comprises at least one of a wetting agent, a suspending agent, and a dispersing agent, or a combination thereof.

57. The formulation of claim 56, wherein said wetting agent is selected from the group consisting of poloxamer, polyoxyethylene ethers, polyoxyethylene sorbitan fatty acid esters (polysorbates), polyoxymethylene stearate, sodium lauryl sulfate, sorbitan fatty acid esters, benzalkonium chloride, polyethoxylated castor oil, and docusate sodium.

58. The formulation of claim 56, wherein said suspending agent is selected from the group consisting of alginic acid, bentonite, carbomer, carboxymethylcellulose, carboxymethylcellulose calcium, hydroxyethylcellulose, hydroxypropyl cellulose, microcrystalline cellulose, colloidal silicon dioxide, dextrin, gelatin, guar gum, xanthan gum, kaolin, magnesium aluminum silicate, maltitol, medium chain triglycerides, methylcellulose, polyoxyethylene sorbitan fatty acid esters (polysorbates), povidone (PVP), propylene glycol alginate, sodium alginate, sorbitan fatty acid esters, and tragacanth.

59. The formulation of claim 56, wherein said dispersing agent is selected from the group consisting of poloxamer, polyoxyethylene sorbitan fatty acid esters (polysorbates) and sorbitan fatty acid esters.

60. The formulation of claim 35, wherein said core further comprises a stiffening agent.

61. The formulation of claim 60, wherein said stiffening agent is cetyl alcohol.

62. A formulation for release of venlafaxine mainly in the colon of a subject, comprising a core that comprises an effective amount of venlafaxine or a pharmaceutically acceptable salt thereof as active ingredient therein and at least one burst controlling agent, wherein said formulation provides a delayed burst release of venlafaxine after at least three hours followed by dispersion of venlafaxine into the blood stream mainly through the colon over a period extending over at least twenty-four hours.

63. A method for treating a subject with venlafaxine, comprising:

administering to the subject a formulation having a therapeutically effective amount of venlafaxine or a pharmaceutically acceptable salt thereof, wherein said formulation provides a substantially sustained plateau of blood concentration level of venlafaxine in the subject, said plateau being at least four hours in length, said formulation comprising:

(a) a core that comprises an effective amount of venlafaxine, wherein said core includes at least one burst controlling agent and a disintegrant, and wherein said core is formed as a compressed tablet; and (b) an outer coating over said core, said outer coating comprising a water insoluble hydrophobic carrier and water-insoluble but hydrophilic particulate matter, contained in the carrier, that forms channels in said outer coating, wherein said channels imbibe liquid and cause said at least one burst controlling agent to burst said coating, thereby releasing venlafaxine in a manner providing a substantially even blood concentration level of venlafaxine for a period extending over at least four hours.

* * * * *